(12) United States Patent
Oliver et al.

(10) Patent No.: US 8,596,126 B2
(45) Date of Patent: Dec. 3, 2013

(54) METHOD AND APPARATUS FOR A RAILWAY WHEEL ULTRASONIC TESTING APPARATUS

(75) Inventors: John R. Oliver, Flossmoor, IL (US); John D. Oliver, Flossmoor, IL (US)

(73) Assignee: Amsted Rail Company, Inc., Chicago, IL (US)

( * ) Notice: Subject to any disclaimer, the term of this patent is extended or adjusted under 35 U.S.C. 154(b) by 359 days.

(21) Appl. No.: 13/135,915

(22) Filed: Jul. 19, 2011

(65) Prior Publication Data
US 2013/0019686 A1    Jan. 24, 2013

(51) Int. Cl.
*G01N 29/26*    (2006.01)

(52) U.S. Cl.
USPC ............................................. 73/620; 73/633

(58) Field of Classification Search
USPC .................................................. 73/620, 633
See application file for complete search history.

(56) References Cited

U.S. PATENT DOCUMENTS

| | | | | |
|---|---|---|---|---|
| 5,574,233 A | * | 11/1996 | Oliver et al. | 73/865.8 |
| 5,864,065 A | * | 1/1999 | Prorok et al. | 73/622 |

* cited by examiner

*Primary Examiner* — John Chapman, Jr.
(74) *Attorney, Agent, or Firm* — Edward J. Brosius

(57) ABSTRACT

A method and apparatus for collecting ultrasonic test data from a railway wheel with an ultrasonic testing apparatus is described. The railway wheel is supported by two drive rollers, each having an indentation which engages with and rotates the wheel. An indexing transducer moves across the rotating wheel, collecting ultrasonic test data while a fixed transducer correlates a reference position on the wheel to the collected test data. To maintain the accuracy of the reference position to the collected test data, it is desirable to maintain the rotational stability of the wheel, minimizing any dynamic instability caused by dimensional tolerances in the wheel. To mitigate instabilities resulting from dimensional tolerances, the indentation of the drive rollers, which engage and drive the flange of the wheel, is adjustable by the flexing design of the drive rollers to maintain frictional contact between the wheel and the drive roller. This allows the indentation to accommodate the varying dimensional tolerances of the wheel flange, mitigating the possibility of dynamic instability resulting from departure of the wheel flange from the indentation.

12 Claims, 7 Drawing Sheets

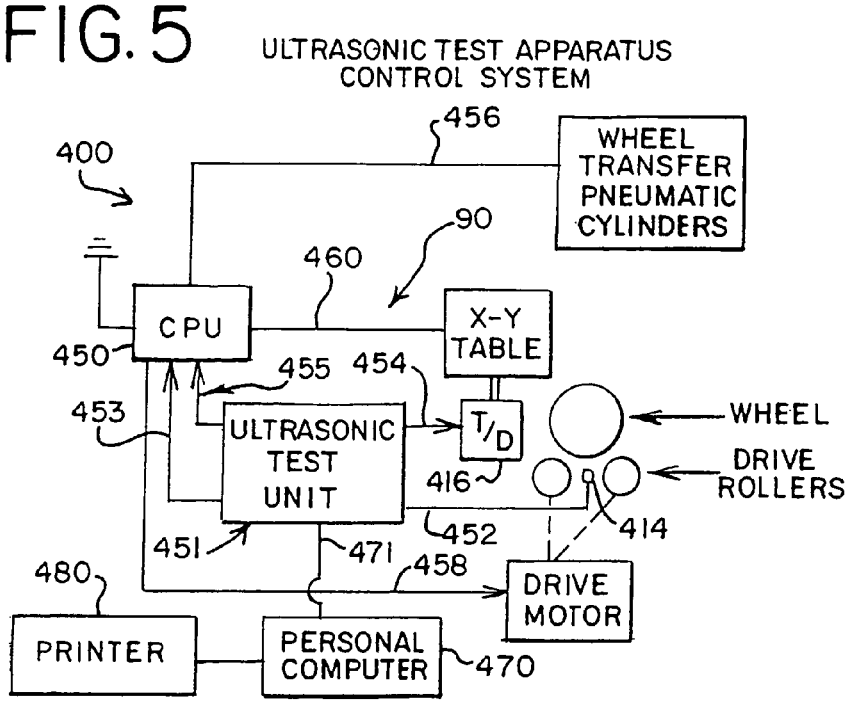
FIG. 5  ULTRASONIC TEST APPARATUS CONTROL SYSTEM
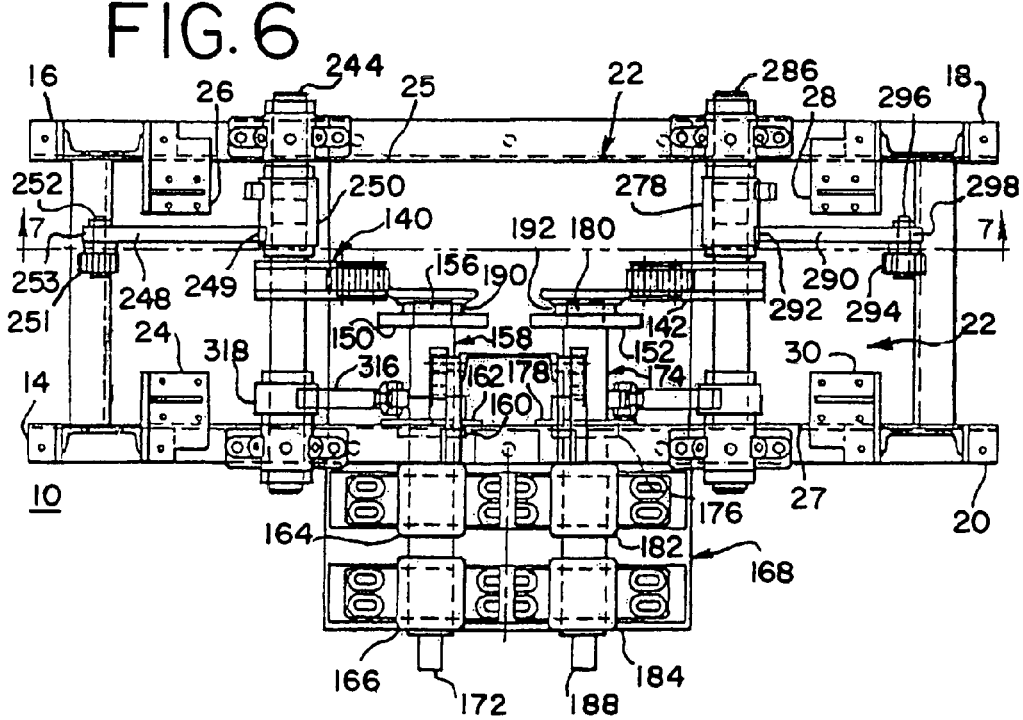
FIG. 6

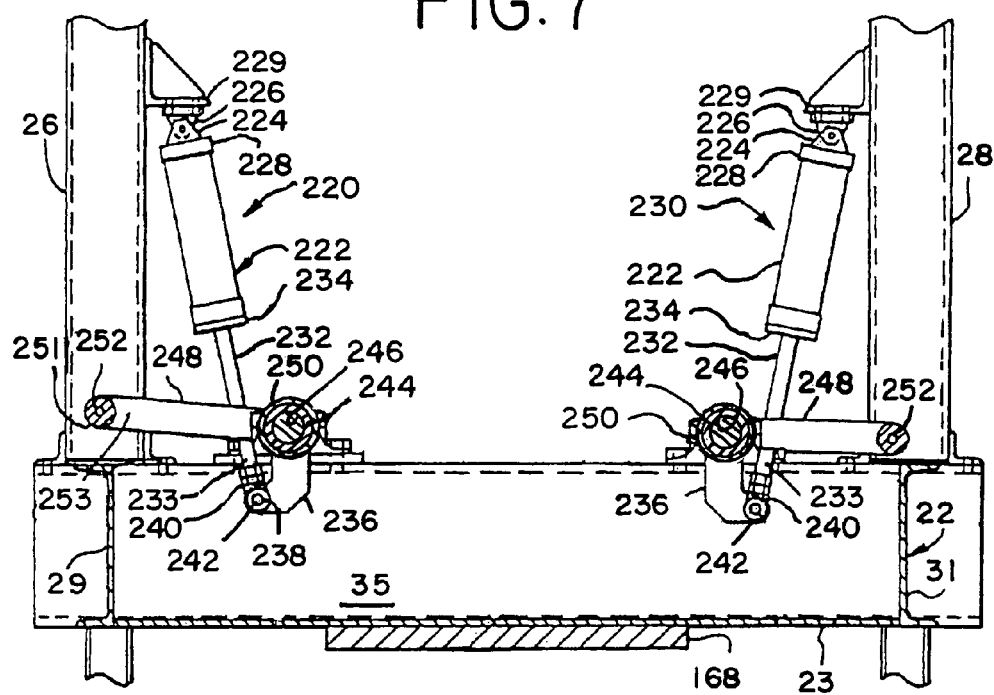
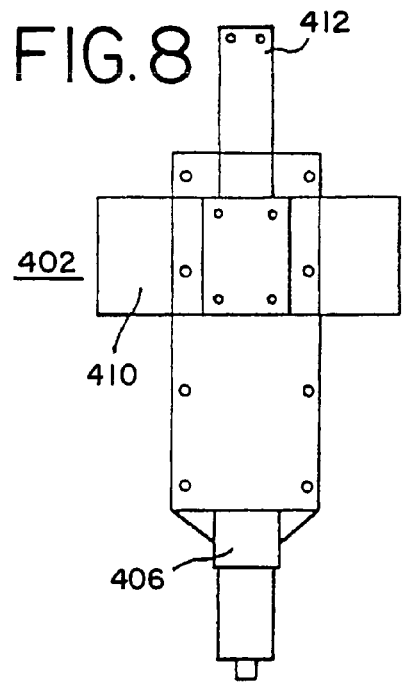
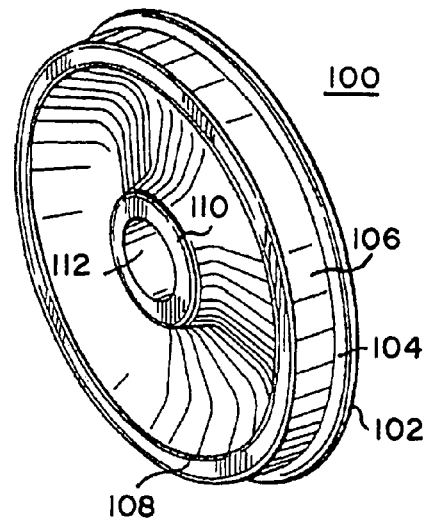

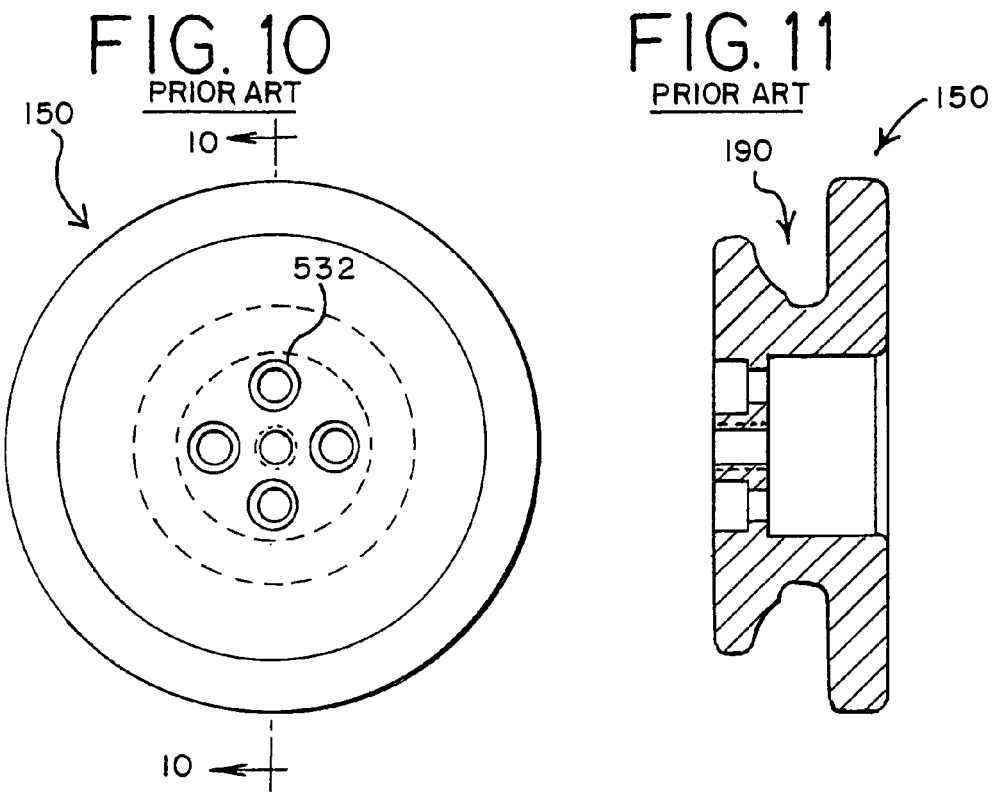
FIG. 10 PRIOR ART
FIG. 11 PRIOR ART
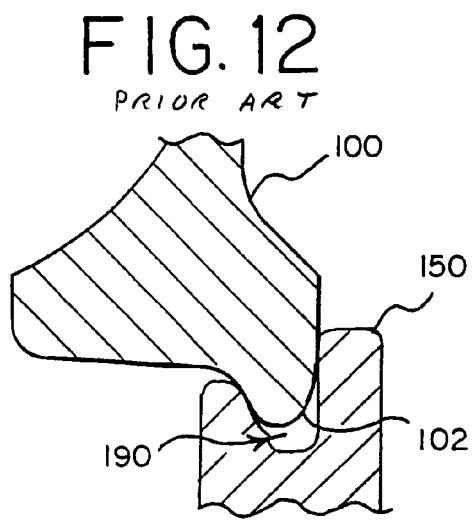
FIG. 12 PRIOR ART

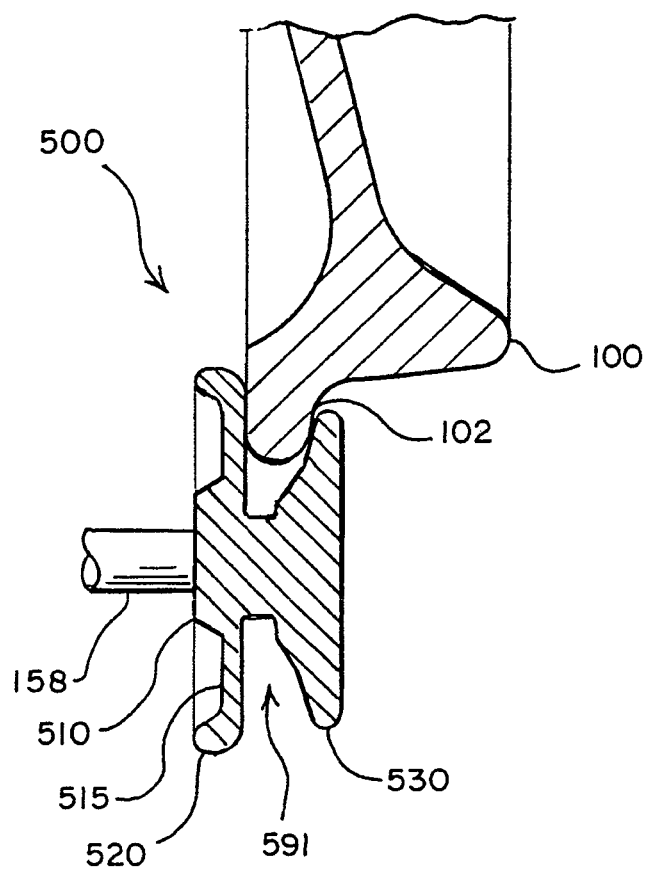

METHOD AND APPARATUS FOR A RAILWAY WHEEL ULTRASONIC TESTING APPARATUS

CROSS REFERENCE TO RELATED APPLICATIONS

This application is related to U.S. Pat. No. 5,864,065, granted Jan. 26, 1999 to Prorok and entitled, "Test Apparatus for a Railway Wheel", which is hereby incorporated by reference in its entirety.

FIELD OF THE INVENTION

This invention relates to ultrasonic testing, and more particularly, in one embodiment, to the ultrasonic testing of railway wheels.

BACKGROUND OF THE INVENTION

Railway wheels are generally either wrought or cast steel, and despite strict quality control measures, may contain flaws resulting from the manufacturing process. These flaws can potentially include voids, cracks, as well as inclusions, which can weaken the wheel and potentially lead to wheel failure. Ultrasound testing has been commonly employed to detect such flaws.

Railway wheels ultrasonically analyzed by fixed position transducers typically examine the wheel and its underlying structure only at discrete, single locations around the perimeter of the wheel tread face or wheel flange. To obtain a more complete diagnostic analysis of the entire wheel structure, without the intensive analysis required by a fixed position transducer, an automated ultrasonic testing method has been developed.

Automated ultrasonic testing has been challenged, to some extent, by the size and weight of railway wheels (typically weighing from 700 to 1000 pounds) which can make the automated collection of accurate ultrasonic test data difficult. Particularly problematic are railway wheels with dimensional tolerances that, although within an acceptable range for production purposes, hamper the automated collection of accurate test data.

In prior art test fixtures, the typical railway wheel may have dimensional tolerances capable of producing dynamic instabilities as the wheel is rotationally driven for ultrasonic examination. These instabilities result in the deflection of the wheel from axial centerline rotation around the geometric center of the wheel in the test fixture. This has proven problematic as the collection of accurate ultrasonic test data often requires maintaining a stable geometric orientation as the wheel rotates.

SUMMARY OF THE INVENTION

A method and apparatus are provided for the application of automated ultrasonic testing to a railway wheel. To achieve faster data collection rates, as well as more accurate and reproducible ultrasonic test data, a novel method and apparatus are presented for mitigating the oscillations and other dynamic instabilities resulting from railway wheel rotation in the ultrasonic test fixture. More specifically, a novel drive assembly in the ultrasonic test fixture adaptively accommodates dimensional tolerances in the rotating railway wheel, dampening deflections and other oscillations that would otherwise potentially affect the accuracy and reproducibility of ultrasonic test data.

BRIEF DESCRIPTION OF THE FIGURES

Various embodiments of the ultrasonic testing apparatus are described and illustrated in the accompanying figures. The figures are provided as examples only and are not intended to be considered as limitations to the invention. Consequently, the ultrasonic testing apparatus and the ultrasonic test fixture are illustrated by way of example and not by limitation in the accompanying figures in which:

FIG. 5 is one embodiment illustrating a control circuit schematic for the exemplary ultrasonic testing apparatus of FIG. 1;

FIG. 6 is a plan view of the ultrasonic testing apparatus illustrated in FIG. 1;

FIG. 7 is an elevation view through section 7-7 of FIG. 6;

FIG. 8 is a plan view of one embodiment of the encoder assembly;

FIG. 9 is an isometric view of an exemplary railway wheel;

FIG. 10 is an orthographic view of one embodiment of an exemplary prior art, unitary drive roller;

FIG. 11 is a cross-sectional view through section 10-10 of the prior art, unitary drive roller depicted in FIG. 10;

FIG. 12 is a partial, cross-sectional view of an exemplary wheel engaging with the exemplary drive roller depicted in FIG. 11;

FIG. 13 is a cross sectional view of one embodiment of an exemplary split drive roller;

DETAILED DESCRIPTION

Although this specification is directed to the testing of railway wheels, it should be understood that the testing apparatus and methods disclosed in this specification are equally applicable to other cast and forged wheels used in industries unrelated to the railway industry. Consequently, the description of the novel method and apparatus as it relates to railway wheels is for convenience only.

Railway Wheel Ultrasonic Testing Apparatus

Figure 1:
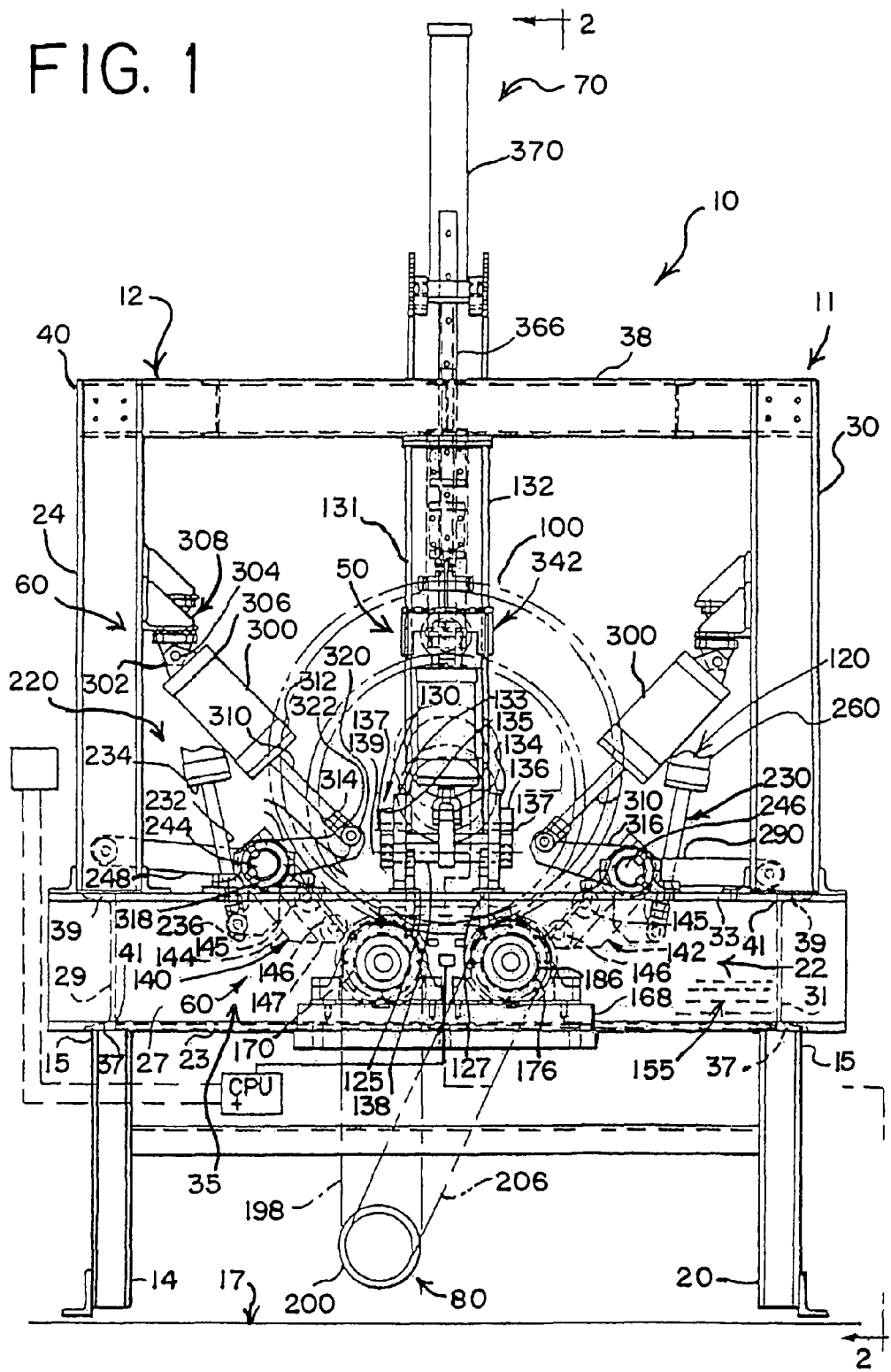
FIG. 1 is a cross-sectional, elevation view of an exemplary embodiment of the ultrasonic testing apparatus.
Figure 2:
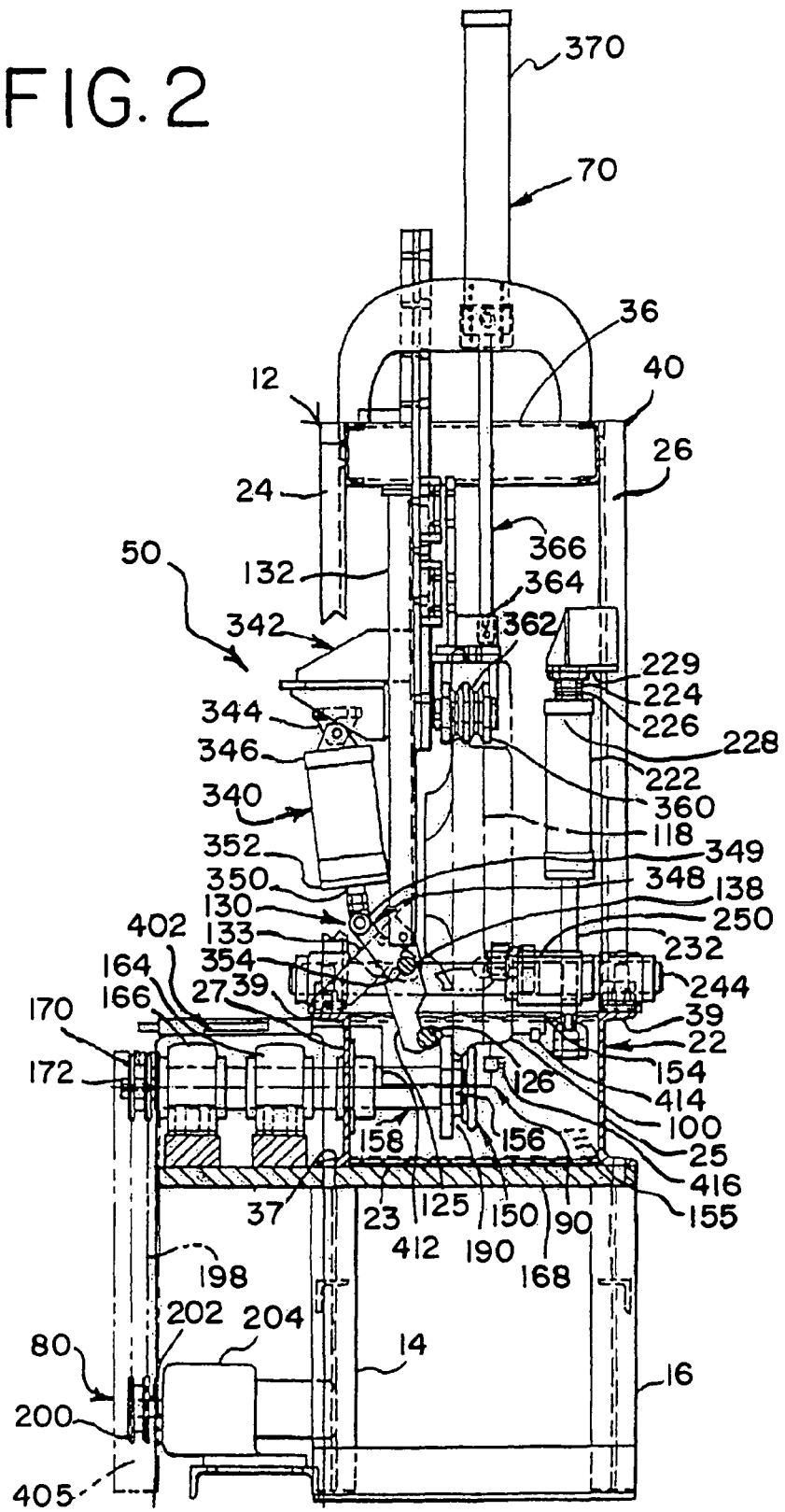
FIG. 2 is a cross-sectional, elevation view through section 2-2 of FIG. 1.

One embodiment of the ultrasonic testing apparatus is depicted in the front elevation view of FIG. 1 and the side elevation view of FIG. 2. The ultrasonic testing apparatus is designed for the nondestructive evaluation and subsurface mapping of the structure of a railway wheel 100 of the type exemplified by the illustration of FIG. 9.

The ultrasonic testing apparatus comprises, in one embodiment, the ultrasonic test fixture 11 for capturing and rotating the wheel and the ultrasonic sensing assembly 90. In addition, a CPU (e.g., a programmable logic circuit (PLC)) (not shown) may be used, in some embodiments, to coordinate the data acquisition activities of the ultrasonic sensing assembly 90 with the wheel handling, transfer, and drive functions performed by the ultrasonic test fixture 11.

The ultrasonic testing apparatus 10 may have many different embodiments that include additional assemblies in various combinations. For example, the extent to which the handling of the railway wheel test specimen is automated will affect the number and types of assemblies required by the test apparatus. In one embodiment, the testing apparatus 10 may include a number of optional assemblies to position and rotate the test specimen in the test fixture 11. These assemblies include, in one embodiment, a transfer assembly 50, a loading assembly 60, a retaining assembly 120, and a restraining assembly 70; in addition to the drive assembly 80 for rotating the test specimen. Each assembly is mounted on, or operable with, in this embodiment, the frame assembly 12 and the coupling fluid tank 22.

As noted above, not all the listed assemblies are required for the collection of ultrasonic test data. For example, in another embodiment, the wheel 100 is placed into position on the drive assembly 80 by a manual device such as a crane and hook (not shown). As a result, the wheel transfer and handling assemblies are not required in this embodiment; instead, only the frame assembly 12, tank 22, and the drive assembly 80 are required in the test fixture 11. Consequently, in one embodiment, the testing apparatus 10 may comprise only the frame assembly 12, the drive assembly 80 for rotating the wheel, the tank 22 for immersing the wheel in a coupling fluid, and the sensing assembly 90 for collecting ultrasonic test data.

Other embodiments of the ultrasonic testing apparatus 10 may include other combinations of assemblies. For example, the tank 22 is not necessary in embodiments where other means for coupling the ultrasonic transducer to the wheel are used (e.g., direct transducer contact in lieu of immersion coupling).

Referring to FIG. 1, the ultrasonic testing apparatus 10 depicts, in one embodiment, an automated system for the collection of ultrasonic test data. The ultrasonic testing apparatus 10 depicted in FIG. 1 has a frame assembly 12 with upright legs 14, 16, 18 and 20 anchored to the floor 17. A tank 22 for holding coupling fluid 155 is mounted on legs 14, 16, 18 and 20 at upper leg ends 15. The tank 22, in one embodiment, is shown with a rectangular shape in FIGS. 1 and 2. The tank 22 is defined by a lower wall 23, front sidewall 25 (shown on FIG. 2), rear sidewall 27, first end wall 29, and second end wall 31. The front sidewall 25, rear sidewall 27, first end wall 29, and second end wall 31 form an upper wall edge 33 and enclose a volume 35. Each sidewall 25, 27 and end wall 29, 31 of the tank 22 has a lower flange 37 and an upper flange 39.

At the corners 41, the ultrasonic testing apparatus 10 has upright arms 24, 26, 28 and 30 extending vertically upward from the tank 22 and upper flanges 39. The upright arms 24, 26, 28 and 30 are connected by horizontal cross braces 36 and 38 at the upper ends 40 of the frame assembly 12.

Railway wheels, although generally similar, may be built to different standards having different dimensions and tolerances. For example, referring to FIG. 9, a typical railway wheel 100 for use in conjunction with the ultrasonic testing apparatus is illustrated. The railway wheel 100 includes a wheel flange 102, flange face 104, tread face 106, rim face 108, and hub 110 with axle bore 112.

Referring back to FIG. 1, a railway wheel 100 is illustrated in dashed outline format in two different sizes to depict the general position of the wheel within the ultrasonic testing apparatus 10. In one embodiment, the ultrasonic testing of a railway wheel begins with the entrance of the wheel 100, rolling on its tread face 106, into frame assembly 12 from left to right in a generally upright manner along a rail track with guide rails (not shown). The wheel 100 moves on the above noted rail and guides to a generally central position in the frame assembly 12 above the tank 22 and among the upright arms 24, 26, 28 and 30 to position the wheel for engagement with the wheel transfer assembly 50.

As wheel 100 is rolled into position, sensors (not shown) communicate a signal indicating the position of the wheel 100. When the wheel reaches a predetermined position in the testing apparatus 10, the lateral retaining assembly 120 is activated, stopping the wheel over the first and the second wheel runway assemblies 140, 142 of the wheel loading assembly 60.

Wheel Retaining Assembly

Referring to FIGS. 6 and 7, the wheel retaining assembly 120 is depicted. The retaining assembly 120 maintains the lateral position of the wheel 100 on the track during testing. For example, in one embodiment, retaining rollers 251 in each of two separate sub-assemblies comprising the retaining assembly 120 are translated by pneumatic cylinders into both the forward and reverse paths of wheel travel on the rail to laterally capture the wheel.

The retaining assembly 120 comprises two separate, but generally identical, mechanical sub-assemblies for blocking each side of the wheel: the first and second retaining roller sub-assemblies 220, 230. The second retaining roller sub-assembly 230, which is in juxtaposed relation to first retaining roller sub-assembly 220, has a mirror image relationship and operation to the first retaining roller sub-assembly 220. In this embodiment, all of the components in the first retaining roller sub-assembly 220 are also present and operate in the same manner as the second retaining roller sub-assembly 230. Consequently, the description and operation of the retaining roller sub-assembly 220 is generally applicable to the operation of the second retaining roller sub-assembly 230. The operation of one of the two retaining roller sub-assemblies in the wheel retaining assembly 120 is described as follows.

A first retaining roller sub-assembly 220 includes a first pneumatic retaining cylinder 222 pivotally coupled to an upright arm 26 with the clevis 224 and first pin 226 at the upper cylinder end 228 and first eye bracket 229. A reciprocable rod 232 is extendable from the pneumatic retaining cylinder 222 at the cylinder lower end 234. A bushing 250 at the second bore 246 has a pivot arm 236 which is coupled to distal end 233 of the reciprocable rod 232 by a second female clevis 240 and a second pin 242. This coupling allows pivotal rotation of the pivot arm 236 on the first pivot shaft 244 (extending through the second bore 246) by the reciprocable rod 232. The stopper arm 248 is coupled to the bushing 250 at the first stopper arm end 249 with the retaining roller 251 secured on the pin 252 at the second stopper arm end 253. Reciprocation of the rod 232 induces rotation of the bushing 250 and the stopper arm 248 to position the retaining roller 251 in proximity to the wheel 100, capturing the wheel 100 in one direction of travel along the track.

In operation, the first and second retaining roller sub-assemblies 220, 230 act together to block lateral travel of the wheel 100 on the track within the ultrasonic testing apparatus 10 with the retaining rollers 251 on either side of the wheel. The retaining roller sub-assemblies 220, 230 are designed to automatically align the wheel 100 in the test fixture 11 with the bridge sub-assembly in preparation for the transfer of the wheel to the loading assembly.

Wheel Transfer Assembly

The wheel 100 initially moves onto the wheel transfer assembly 50, and more specifically, into the downwardly extending arms 125, 127 and second pin 126 of the bridge sub-assembly 130. With the wheel 100 retained in place with the wheel retaining assembly 120, the bridge sub-assembly 130 of the wheel transfer assembly 50 transfers the wheel 100 into the wheel loading assembly 60. The operation of one embodiment of the wheel transfer assembly 50 and its component parts is described in more detail below.

The wheel transfer assembly 50 depicted in FIGS. 1 and 2 has a first upright support 131 and a second upright support 132 downwardly extending from the horizontal brace 38.

Upwardly extending angle brackets 133, 134 are mounted on the rear sidewall 27 and are connected to the upright supports 131, 132 respectively. Anchoring braces 135 and 136 are positioned on the outer surfaces of the angle brackets 133, 134 (respectively) with securing bolts 137 extending through braces, brackets, and supports 131 to 136. A cross pin 138 extends through braces 135, 136 and angle brackets 133, 134 with first and second downwardly extending arms 125 and 127, respectively. Second pin 126 extends between the downwardly extending arms 125 and 127.

Wheel transfer assembly 50 in FIGS. 1 and 2 has pneumatic transfer cylinder 340 secured at its upper end 346 by an eye bracket 342 of the clevis 344. The eye bracket 342 is mounted on the first and second upright supports 131 and 132. The connecting arm 348 is pivotally connected at its first end 349 to the drive rod 350 at the lower end 352 of the pneumatic transfer cylinder 340 and is drivingly coupled to the cross pin 138 at the lower end 354 of the connecting arm 348.

After engaging the wheel in position on the bridge sub-assembly 130, the pneumatic transfer cylinder 340 is actuated to rotate the bridge assembly 130. This occurs with the extension of the drive rod 350 by the pneumatic transfer cylinder 340, rotating the connecting arm 348 and cross pin 138, which consequently rotates the downwardly extending arms 125 and 127 about the pin axis 139, and thereby deposits the wheel 100 on, or captures wheel from, the wheel loading assembly 60. This locates the wheel 100 on the first and second wheel runway sub-assemblies 140, 142 of the wheel loading assembly 60.

Wheel Loading Assembly

After the wheel transfer assembly 50 has positioned the wheel 100 for engagement with the first and second wheel runway sub-assemblies 140, 142, the wheel loading assembly 60 lowers the wheel 100 to engage with the drive rollers 150, 152 of the drive assembly 80. The wheel runway sub-assemblies in the wheel loading assembly 60 are part of two separate and independent sub-assemblies comprising the wheel loading assembly 60. These two sub-assemblies are generally identical in structure and operation, juxtaposed on either side of the wheel in the test fixture 11. Because the two wheel runway sub-assemblies 140, 142 operate similarly, as though mirror images, only the structure and operation of wheel runway sub-assembly 140 will be described.

One embodiment of the wheel loading assembly 60 is illustrated in FIG. 1. In this embodiment, the wheel is supported by the loading rollers 145, 146 in both wheel runway sub-assemblies 140 and 142. The wheel runway sub-assemblies 140, 142 are immediately adjacent and equally support the wheel 100 centered above the runway sub-assemblies. The wheel runway sub-assemblies 140, 142 rotatably pivot downward in an arc to lower the wheel 100 between the runway sub-assemblies onto the drive rollers of the drive assembly 80.

The operation of the wheel runway sub-assembly 140 is powered by a pneumatic loading cylinder 300. The pneumatic loading cylinder 300 is pivotally coupled to the upright arm 24 with a clevis 302 and pin 304 at the upper cylinder end 306 and the third eye bracket 308. A reciprocable rod 310 with a distal end 314 is extendable from the lower end 312 of the pneumatic loading cylinder 300 and is coupled to the pivot arm 316 at the pivot arm end 322 by a bushing 320 and a pin 324. The pivot arm 316 at its second end 319 is secured to a bushing 318 on the first pivot shaft 244 at its second end.

The first wheel runway sub-assembly 140 in FIG. 1 has a runway arm 144 with a first loading roller 145 and a second loading roller 146 at its distal end 147. The runway arm 144 is also secured to the first pivot shaft 244 and is rotatable by movement of the pivot arm 316 to align the loading rollers 145, 146 with the track (not shown) to receive wheel 100.

Similarly, the second wheel runway sub-assembly 142 has a second set of loading rollers 145, 146 to receive and transfer the wheel 100 either into or out of the ultrasonic testing apparatus 10. As noted above, the second wheel runway sub-assembly 142 is juxtaposed to the first wheel runway assembly 140, consequently, the direction of rotation of the reciprocating shafts and pivoting of the several components are mirror images of the direction of movement of the components of the wheel runway sub-assembly 140.

Using the wheel loading assembly 60, the first and second loading rollers 145, 146 of wheel runway sub-assemblies 140 and 142 lower the wheel 100 onto the drive rollers 150, 152 (see FIG. 6) of the drive assembly 80. Thereafter, the wheel runway sub-assemblies 140, 142 are moved away from contact with the wheel 100. The wheel runway sub-assemblies 140, 142 are rotated away from the wheel 100 by extending the rods 310 from the pneumatic loading cylinders 300, which move pivot arms 316 on first pivot shaft 244 away from the wheel.

Wheel Vertical Restraining Assembly

In addition to restraining the lateral motion of the wheel 100 in the testing apparatus 10, it is also desirable, in certain embodiments, to support the upper portion of the wheel 100 to prevent an overturning moment. The wheel vertical restraining assembly 70 performs this function.

Referring to FIG. 2, after the wheel 100 is transferred to the loading assembly 60, the wheel vertical restraining assembly 70 is in position to capture the top of the wheel 100 in the indentation 362 of the restraining roller 360. The restraining roller 360 is mounted on the distal end 364 of the rod 366 and is moved into position at the upper end of the wheel 100 in the frame assembly 12 by extending the rod 366 from the pneumatic restraining cylinder 370. The pneumatic restraining cylinder 370 is mounted generally between cross-braces 32, 34, 36 to 38 at the upper end 40 of the frame assembly 12. The indentation 362 of the restraining roller 360 captures the top end of the wheel 100 within the frame assembly 12, maintaining the wheel in an upright position during the test cycle.

The wheel 100 is now, in this embodiment, captured both vertically and laterally (on the track). With the wheel 100 in engagement with the first and second drive rollers 150, 152, the drive assembly 80 is available to rotate the drive rollers 150, 152, and in turn, rotate the wheel 100.

Wheel Drive Assembly

Referring to FIGS. 2 and 6, the drive assembly 80 includes the first and second drive rollers 150, 152 which, in one embodiment, are positioned in the tank 22 below the fluid surface 154 of the coupling fluid 155. The first drive roller 150 and second drive roller 152 each have an arcuate indentation 190, 192, respectively, on each drive roller circumference. The indentations 190, 192 of the first drive roller 150 and the second drive roller 152 are aligned to engage a portion of the wheel flange of the wheel 100 during testing. The indentations 190, 192 engage with the wheel flange 102 to rotate the wheel 100.

The first drive roller 150 is mounted on the first end 156 of the first drive shaft 158. The first drive shaft 158 extends through the first aperture 160 and the first seal 162 in the rear sidewall 27 of the tank 22 and through the first and the second pillow block and bearing 164, 166 respectively. The first and the second pillow block and bearing 164, 166 are mounted on the bearing plate 168, which is secured to the frame assembly 12. Affixed to the first drive shaft 158 is a first driven sprocket 170 mounted on the second end 172 of the first drive shaft 158.

Juxtaposed to the first drive roller 150 is the second drive roller 152 on the first end 180 of the second drive shaft 174. The second drive shaft 174 in FIG. 6 is generally parallel to the first drive shaft 158 and extends through the second aperture 176 and seal 178 in the tank 22. Second drive shaft 174 continues to extend through the third and forth pillow block and bearing 182 and 184 respectively. The third and fourth pillow block and bearing 182 and 184 are mounted on bearing plate 168. Affixed to the second drive shaft 174 is a second driven sprocket 186 (shown on FIG. 1) mounted on the second end 188 of the second drive shaft.

Referring back to FIG. 1, the wheel drive assembly 80 also includes drive chain 198 which extends between the first driven sprocket 170 and the driver sprocket 200. The driver sprocket 200 is affixed to the motor shaft 202 extending from the drive motor 204. Similarly, the second drive chain 206 extends between the driver sprocket 200 and the second driven sprocket 186. The wheel 100 may be rotated by driving rotation of any or both the first driven sprocket 170 or the second driven sprocket 186 from the drive motor 204 rotating the driver sprocket 200 and connecting drive chains 198, 206.

In an alternate embodiment a second drive motor (not shown) with a separate drive sprocket (not shown) may be utilized for independent coupling to the second driven sprocket 186. Other types of drives could also be provided; including, for example, belts and sheaves, and gear drives. Alternatively, in another embodiment, second driven sprocket 186 and second drive shaft 174 may act as an idler or roller without direct coupling to a drive motor; using the second roller 152 as an idler for wheel support only.

Referring to FIG. 10, an orthographic view of an exemplary embodiment of a prior art, drive roller 150 is illustrated having a plurality of shaft fastener bores 532. The shaft fastener bores align with bores in the drive shaft (not shown) to allow the drive roller 150, in this embodiment, to be affixed to the drive shaft with threaded fasteners (not shown).

Referring to FIG. 11, a cross-sectional view of the drive roller 150 depicted in FIG. 10 is illustrated. An indentation 190 for capturing the wheel flange of the wheel is formed around the circumference of the drive roller 150. In the embodiment illustrated in FIGS. 10 and 11, the drive roller 150 is a unitary component.

Referring to FIG. 12, the engagement of the wheel 100 with the indentation 190 of the drive roller 150 is illustrated. The drive roller 150 imparts rotational motion to the wheel 100 through frictional interaction between the indentation 190 of the drive roller 150 and the wheel flange 102 captured in the indentation. This frictional fit and the effectiveness of the ultrasonic testing apparatus 10 in general, are highly dependent upon the dimensional tolerances of the wheel 100.

In practice, large variations in the dimensional tolerances of the wheel 100, particularly at high rotational velocities, may create dynamic instabilities causing the wheel 100 to depart from the indentations in the drive rollers. Data collection accuracy is degraded as a result of instabilities in rotational motion produced by the erratic movement of the wheel. To mitigate oscillations and dynamic instabilities resulting from dimensional tolerances in the wheel, an alternative and novel embodiment of the drive rollers is described below.

Referring to FIG. 13, a cross-sectional view of an exemplary and novel drive roller embodiment (referred to hereinafter as a drive roller 500) is illustrated. The drive roller 500, in one embodiment, is comprised of a single piece structure 510 which is fitted on the end of drive shaft 158.

Drive roller structure 510 is itself comprised of an inner annular section 520 and an outer annular section 530. A gap 591 is formed between inner annular section 520 and outer annular section 530. Flange 102 of railway wheel 100 is fitted into gap 591. Inner annular section 520 may include a cutout area 515 which reduces the rigidity of a inner annular section 520 to allow inner annular section 520 to flex and adjust the width of gap 591 to accommodate varying sizes and design of railway wheel flanges 102. Drive roller structure 510 may be comprised of a steel or a structural plastic; in either case being designed to have adequate strength and wear resistance to impact rotation to railway wheel 100 while having a long service life.

Ultrasonic Sensing Assembly

Referring to FIG. 5, a control schematic 400 of the ultrasonic testing apparatus control system is illustrated which includes, in one embodiment, the ultrasonic sensing assembly 90. The ultrasonic sensing assembly 90 comprises, in one embodiment, the ultrasonic test unit, transducers, and encoder assembly for transmitting and receiving, as well as processing ultrasonic signals.

Ultrasonic Transducers

Ultrasonic transducers transmit ultrasonic signals to the test specimen (i.e., the wheel 100) and receive reflected ultrasonic signals. The reflected ultrasonic signals provide the data necessary to allow analysis and detection of substructure flaws in the wheel. In one embodiment of the ultrasonic sensing assembly 90, two transducers may work together to map the position of flaws in the test specimen.

Figure 4:
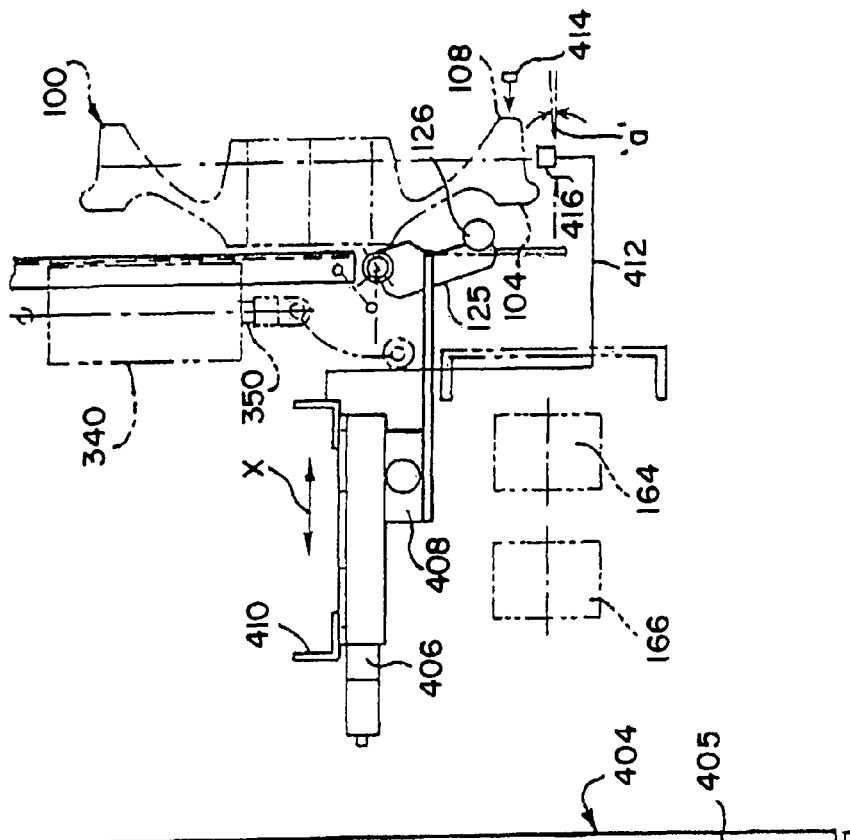
FIG. 4 is a side elevation view of the encoder assembly of FIG. 3.

A fixed transducer 414 is provided in a fixed location in close proximity to the wheel rim face 108 as noted in FIG. 4 to provide a reference position. The other transducer is an indexing transducer 416 which moves relative to the wheel 100 in close proximity to the tread face 106. To move the indexing transducer 416 relative to the wheel 100, an encoder assembly 402 is used to move the indexing transducer 416 in fixed increments to traverse the wheel 100.

Encoder Assembly

Figure 3:
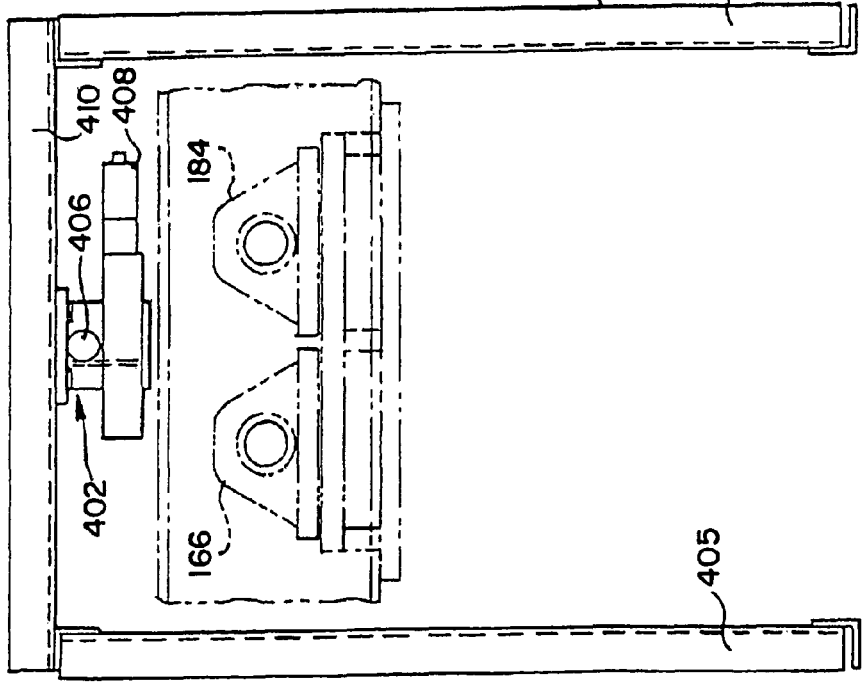
FIG. 3 is a front elevation view of the mounting stand and encoder assembly of the ultrasonic testing apparatus depicted in FIG. 1.

In this embodiment, the encoder assembly 402 (as illustrated in FIGS. 3, 4, and 8) is affixed to mounting stand 404 and functions to move and record the position of the indexing transducer 416 as it moves incrementally across the wheel in discrete steps. The encoder assembly synchronizes data acquisition with the indexing transducer's position, allowing the ultrasonic testing apparatus to accurately identify the location and the dimensions of defects found in the scan. Encoder assembly 402 includes the transducer drive motors 406, 408; control table 410; and transducer arm 412. Each of these components of the encoder assembly 402 are described below in more detail.

Transducer Drive Motors

The mounting stand 404 to which the encoder assembly 402 is attached, is anchored to the floor 17 as noted in FIGS. 2 and 3. The encoder assembly 402 is affixed to the mounting stand 404 (above the pillow blocks and bearings 164, 166, 182, and 184) with first or x-direction transducer drive motor 406 and second or y-direction transducer drive motor 408 secured to the control table 410 at the top of the mounting stand 404. In this configuration, the control table 410 and the transducer arm 412 are movable in the x direction by the first transducer drive motor 406 (horizontally along the plane as noted in FIG. 4). Similarly, a second transducer drive motor 408 is operable to move the control table 410 in the y-direction as noted in FIG. 3. The transducer drive motors 406, 408 may be, in one embodiment, micro-stepper motors.

Referring to FIG. 4, the transducer arm 412 is driven by the control table 410. At its distal end, the transducer arm 412 has an indexing transducer 416. The transducer arm 412, in this embodiment, has a generally L-shaped form extending downwardly into the coupling fluid 155 of tank 22. The indexing transducer 416 is driven in incremental steps by the transducer drive motors 406, 408 through the control table 410 and transducer arm 412. With the indexing transducer 416 controlled by the encoder assembly 402 and the fixed transducer 414 positioned adjacent to the wheel, the transducers are ready to transmit and receive ultrasonic signals under the control of the ultrasonic test unit.

Ultrasonic Testing Unit

Referring back to FIG. 5, the ultrasonic test unit 451, in one embodiment, controls the transducers 414, 416 including the frequency, voltage (or more generally the power of the ultrasonic signal emitted by the transducer), pulse repetition rates, filter selections, etc. The ultrasonic testing unit 451 also receives ultrasonic test data from the transducers 414, 416.

In one embodiment, the ultrasonic test unit 451 also provides input and output ports (e.g., USB ports) to provide communication capabilities directly to a personal computer 470 which is connected to a printer 480. The personal computer 470 functions as a workstation for the operator, allowing the monitoring of data collection as well as providing the capability to perform further analysis on the collected data. The personal computer 470 may include software for processing collected data, provide alarm monitoring functions, as well as advanced imaging functions for displaying the ultrasonic data.

For example, in one embodiment, fixed transducer 414 communicates a signal to ultrasonic test unit 451 through line 452, which is further communicated and stored in the personal computer 470 through line 471. Similarly, indexing transducer 416 communicates a signal to the ultrasonic test unit 451 through line 454, which is also communicated and stored in the personal computer 470 for comparison and evaluation through line 471.

Ultrasonic Testing Apparatus Control

The electrical control schematic depicted in FIG. 5 illustrates one embodiment of the operation and control of the ultrasonic testing apparatus 10. The ultrasonic testing apparatus 10 has an ultrasonic sensing assembly 90 operating in cooperation with a CPU 450 which coordinates the ultrasonic sensing assembly 90 with the wheel handling capabilities of the ultrasonic test fixture 11 (through control of the pneumatic cylinders).

For example, in some embodiments, CPU 450 is operable as a programmable logic controller (PLC) to provide control signals through lines 456 to the pneumatic cylinders of ultrasonic test fixture 11 for delivery and transfer of wheel 100 to and from frame assembly 12. These pneumatic cylinders are present in the lateral retaining assembly, the vertical restraining assembly, the transfer assembly, and the loading assembly. CPU 450 controls each of the pneumatic cylinders in the above assemblies to position the wheel in the testing apparatus 10. A number of position sensors (not shown), in communication with CPU 450, trigger the appropriate handling sequence in the CPU 450 as the wheel 100 is initially positioned in the test fixture 11. The ultrasonic testing apparatus 10 is controlled by software programming executed by CPU 450.

In other embodiments, however, the drive assembly may be the only wheel handling mechanism present in the ultrasonic testing apparatus (i.e., no pneumatic cylinder controls are necessary). In some embodiments, the CPU 450 is still required to control the encoder assembly 402, indexing transducer 416, as well as the transducer drive motors 406, 408. Consequently, the CPU 450 is also part of the ultrasonic sensing assembly 90 in some embodiments.

In addition to controlling the pneumatic cylinders, the CPU 450 also controls the operation of the drive motor 204 in the drive assembly 80 to rotate the test specimen. Once the test specimen is engaged with the drive assembly 80, the CPU 450 may also, in one embodiment, communicate control signals through line 458 to start drive motor 204 for timed rotation of wheel 100 in frame assembly 12.

CPU 450, in one embodiment, also coordinates control of portions of the ultrasonic sensing assembly 90, including the encoder assembly for indexing transducer 416. In this embodiment, CPU 450 may provide control signals to transducer drive motors 406 and 408 through line 460 to index transducer 416. In still other embodiments, the encoder assembly 402 and the CPU 450 are not necessary in non-automated, ultrasonic data collection activities.

The signal from the fixed transducer 414 provides a reference point for noting the relative location of the defects in the wheel 100 which are recorded with indexing transducer 416. In one embodiment, signals from the indexing transducer 416 and the fixed transducer 414 may be communicated through lines 454 and 452 respectively to the CPU 450 through lines 455 and 453 to assist in the control of the test fixture 11 and the appropriate handling and transfer of the wheel.

Phase Array Ultrasonic Testing

If desired, more advanced ultrasonic test instrumentation may be used, including, phase array ultrasonic testing. In one embodiment, the ultrasonic test unit 451 may be a phase array ultrasonic unit, capable of more precise control of transmitted and received ultrasonic signals from a phase array transducer. In one embodiment, the phase array ultrasonic unit includes a pulser/receiver board (not shown) for transmitting and receiving ultrasonic signals and a multiplexer (not shown) for addressing the multi-element, phase transducers (not shown).

The phase array transducers have multi-element construction to allow the ultrasonic test unit 451 to individually address and activate specific elements in the transducer to produce a dynamically controlled aperture having a calculated distribution of individually activated elements. These programmable apertures are customized for each region of interest in the test specimen, providing the capability to focus ultrasonic energy at an angle and depth in a way that maximizes the clarity of the visual representation of the test specimen in that region. A transmitting phase array transducer (i.e., a transmitting aperture) and a receiving phase array transducer (i.e., a receiving aperture) may work together with independently selected receiving and transmitting angles at a predetermined focal length to develop the image desired in the test specimen at the region of interest.

Baseline Data Collection

Initial set-up of the CPU 450 and the ultrasonic test unit 451 includes the development of a baseline ultrasonic test measurement of a reference wheel having the same size as the wheels to be tested. The data collected from the reference railway wheel provides a baseline set of empirical reference parameters for the comparison and evaluation of test data collected with the transducers 414, 416 from the test specimen.

Test Specimen Data Collection

Wheel 100, supported on the drive rollers 150, 152, is in position for test and evaluation of the subsurface of the wheel tread face 106. In this position, the wheel 100 may be rotated as noted above by actuation of the drive motor 204.

Initially the relative position of the second or indexing transducer 416, in one embodiment, is set by a signal sensed by the first or fixed transducer 414 on the rim face 108 in FIG. 4. This relative position signal is communicated to the CPU 450 from the ultrasonic test unit 451 on line 452 and is utilized to compare the rim face 108 to the reference wheel data to position second transducer 416. The position of the second or indexing transducer 416 is based upon the baseline empirical data from the reference wheel. This evaluation then locates the centerline 118 of tread face 106, which determines the travel distance of the indexing transducer 416 from the rim face 108 toward the wheel flange 102.

However, in this embodiment, the second or indexing transducer 416 is displaced from the horizontal by an acute angle "a" in FIG. 4. The acute angle "a" is the slope of the angular displacement of the tread face 106 from a horizontal plane. This slope or taper is thereby accommodated by the test fixture to maintain the indexing transducer 416 at a normal or facing relationship to the tread face 106.

In one embodiment, the initial position of the transducer 416 is a displacement from the rim face 108 toward centerline 118 (see FIG. 2) of the wheel 100. Thereafter, the wheel 100 is rotated with drive rollers 150, 152. As the wheel 100 rotates, a transducer drive motor 406, in one embodiment, incrementally indexes the indexing transducer 416 toward the wheel flange 102. The transducer drive motor 406 moves the arm 412 and with it, the indexing transducer 416.

In one embodiment, the transducer 416 is indexed along the tread face 106 from the rim face 108 to the wheel flange 102 at a rate of approximately 0.075 inches of lateral travel per wheel revolution, providing a travel range of about 0.675 inches along the surface of the tread face 106. In one embodiment, the wheel 100 is rotated through nine revolutions at a predetermined rate. The number of wheel revolutions, however, may be varied by the operator to accommodate wheel size variations or other variables.

As the indexing transducer indexes over the wheel, an ultrasonic signal is communicated through the coupling fluid 155 in the tank 22 to the tread face 106 to analyze the subsurface for various discontinuities or flaws such as cracks, voids, and inclusions. Any of the above anomalies may result in a discontinuity exemplified by the presence of a reflected signal detected by the indexing transducer 416.

The reflected signal, which may be analogized to a reflected radar signal, provides a comparative signal to the baseline empirical data. Failure of the signal to provide indication of a sound wheel structure may result in further testing and evaluation, repair, or rejection of the wheel as scrap. In the case of a signal in excess of a predetermined value, the computer can provide an alarm or other signal to indicate an unacceptable product or indicate the requirement for rerunning the test.

The test apparatus described above, in one embodiment, tracks the precise location of any discontinuities by recording a reference position on the wheel. With this data, the novel testing apparatus not only provides a practical means to provide a comprehensive test of the tread face, but also a methodology for developing a predictive maintenance program using a historical database of ultrasonic signatures to detect incipient failures. Furthermore, the novel testing apparatus provides an opportunity to evaluate newly manufactured railway wheels to verify the structural integrity, as well as providing a check on the effectiveness of the quality control processes implemented during the manufacturing process.

While the invention has been illustrated with respect to several specific embodiments, these embodiments are illustrative rather than limiting. Various modifications and additions could be made to each of these embodiments as will be apparent to those skilled in the art. Accordingly, the invention should not be limited by the above description or of the specific embodiments provided as examples. Rather, the invention should be defined only by the wing claims.

The invention claimed is:

1. An ultrasonic test fixture for a wheel, comprising:
a plurality of drive rollers for supporting the wheel, wherein at least one of the plurality of drive rollers comprises:
a unitary structure having a first annular section affixed around a drive shaft, and
a second annular section, the second annular section adjacent to the first annular section to form an indentation between the first annular section and the second annular section for engaging the wheel;
the first annular section having a flexibility such that the indentation between the first annular section and the second annular section is adjustable to accommodate varying sizes of wheels,
a drive motor connected to the drive shaft to rotate the at least one of the plurality of drive rollers.

2. The ultrasonic test fixture of claim 1, further comprising a bore through the first annular section, wherein a threaded fastener extends through the bore.

3. The ultrasonic test fixture of claim 1, further compromising a tank.

4. The ultrasonic test fixture of claim 3, further comprising a frame assembly, wherein the tank is mounted to the frame assembly, and further wherein the plurality of drive rollers are mounted inside the tank.

5. The ultrasonic test fixture of claim 4, further comprising a restraining roller mounted to the frame assembly, the restraining roller for selectively engaging the wheel to maintain the vertical orientation of the wheel on the plurality of drive rollers.

6. The ultrasonic test fixture of claim 3, wherein the plurality of drive rollers are mounted inside the tank, and further wherein the tank contains a coupling fluid.

7. An ultrasonic test fixture for a wheel, comprising:
a plurality of drive rollers for supporting the wheel, at least one of the plurality of drive rollers for rotating the wheel, wherein at least one of the plurality of drive rollers comprises:
an inner annular section affixed to a drive shaft;
and an adjacent outer annular section to form an indentation between the inner annular section and the outer annular section for engaging the wheel;
one of the annular sections is axially displaceable relative to the other annular section to vary the indentation and accommodate varying sizes of wheels, and
a drive motor connected to the drive shaft to rotate at least one of the drive rollers.

8. The ultrasonic test fixture of claim 7, further comprising: a first bore through the drive roller to accept the drive shaft.

9. The ultrasonic test fixture of claim 7, further compromising a tank for holding a coupling fluid.

10. The ultrasonic test fixture of claim 9, further comprising a frame assembly, wherein the tank is mounted to the frame assembly, and further wherein the plurality of drive rollers are mounted inside the tank.

11. The ultrasonic test fixture of claim 10, further comprising a restraining roller mounted to the frame assembly, the restraining roller for selectively engaging the wheel to maintain the vertical orientation of the wheel on the plurality of drive rollers.

12. The ultrasonic test fixture of claim 7, further comprising a tank for holding a coupling fluid, wherein at least one of the drive rollers are mounted inside the tank.

* * * * *